United States Patent
Gazza

(10) Patent No.: US 8,268,418 B2
(45) Date of Patent: Sep. 18, 2012

(54) CATHETER BALLOONS

(75) Inventor: Gianluca Gazza, Monaco (IT)

(73) Assignee: Medtronic, Inc., Santa Rosa, CA (US)

( * ) Notice: Subject to any disclaimer, the term of this patent is extended or adjusted under 35 U.S.C. 154(b) by 1496 days.

(21) Appl. No.: 10/478,161

(22) PCT Filed: Oct. 17, 2003

(86) PCT No.: PCT/IB03/04584
§ 371 (c)(1),
(2), (4) Date: Nov. 17, 2003

(87) PCT Pub. No.: WO2005/037337
PCT Pub. Date: Apr. 28, 2005

(65) Prior Publication Data
US 2005/0096690 A1    May 5, 2005

(51) Int. Cl.
*B32B 1/08* (2006.01)
*B32B 27/34* (2006.01)
*A61M 25/00* (2006.01)

(52) U.S. Cl. ............... 428/35.2; 428/35.5; 428/36.9; 604/96.01; 604/264; 604/915

(58) Field of Classification Search ............ 428/35.2, 428/35.5, 36.9; 604/915, 96.01, 264; 206/571, 206/364
See application file for complete search history.

(56) References Cited

U.S. PATENT DOCUMENTS

| | | | | |
|---|---|---|---|---|
| 3,660,356 A | * | 5/1972 | Radlmann et al. | 28/292 |
| 4,115,475 A | * | 9/1978 | Foy et al. | 525/425 |
| 4,346,024 A | * | 8/1982 | Coquard et al. | 524/219 |
| 4,593,076 A | * | 6/1986 | Russo et al. | 525/425 |
| 5,556,383 A | | 9/1996 | Wang et al. | |
| 5,644,020 A | * | 7/1997 | Timmermann et al. | 528/288 |
| 5,703,177 A | * | 12/1997 | Hoff | 525/411 |
| 5,951,941 A | * | 9/1999 | Wang et al. | 264/523 |
| 6,077,900 A | * | 6/2000 | Boudreaux et al. | 524/501 |
| 6,100,370 A | * | 8/2000 | Hoff et al. | 528/310 |
| 6,200,290 B1 | * | 3/2001 | Burgmeier | 604/96.01 |
| 6,284,333 B1 | * | 9/2001 | Wang et al. | 428/35.5 |
| 6,406,457 B1 | * | 6/2002 | Wang et al. | 604/96.01 |
| 6,552,160 B2 | * | 4/2003 | Pavlin | 528/339.5 |
| 6,592,550 B1 | * | 7/2003 | Boatman et al. | 604/103.06 |
| 6,608,169 B2 | * | 8/2003 | Abe | 528/310 |
| 6,881,209 B2 | * | 4/2005 | Boatman et al. | 604/525 |
| 7,029,732 B2 | * | 4/2006 | Wang et al. | 428/1.6 |

(Continued)

FOREIGN PATENT DOCUMENTS

DE    19933279    3/2001

(Continued)

OTHER PUBLICATIONS

International Search Report for PCT/IB2003/004584 filed on Oct. 17, 2003 in the name of Bayco Consulting Limited.

(Continued)

*Primary Examiner* — Michele L Jacobson

(57) ABSTRACT

The invention relates to a balloon for medical devices, in particular for catheters used in angioplasty, comprising a polyamide copolymer material characterized in that said polyamide copolymer material is represented by the general formula (I):

HO—(PF—OOC—PA-COO—PF—COO—PA)$_n$-COOH in which PA is a polyamide segment and PF is a diol segment comprising dimer diols and/or corresponding OH-terminating diol polyesters and n is a number between 5 and 20.

22 Claims, 1 Drawing Sheet

U.S. PATENT DOCUMENTS

| | | | |
|---|---|---|---|
| 7,101,597 B2 * | 9/2006 | Wang et al. | 428/35.2 |
| 7,108,826 B2 * | 9/2006 | Wang et al. | 264/573 |
| 7,163,522 B1 * | 1/2007 | Wang et al. | 604/96.01 |
| 7,166,680 B2 * | 1/2007 | DesNoyer et al. | 525/425 |
| 7,220,816 B2 * | 5/2007 | Pacetti et al. | 528/272 |
| 7,264,458 B2 * | 9/2007 | Holman et al. | 425/174.4 |
| 2005/0065314 A1 * | 3/2005 | Lai | 528/271 |
| 2007/0249789 A1 * | 10/2007 | Buehler et al. | 525/420 |

FOREIGN PATENT DOCUMENTS

| | | |
|---|---|---|
| DE | 19933279 A1 | 3/2001 |
| EP | 0921832 A1 | 6/1999 |
| EP | 1219310 | 7/2002 |
| EP | 1219310 A2 | 7/2002 |
| EP | 0921832 | 1/2004 |
| EP | 1 673 114 B1 | 7/2008 |
| WO | 9604952 | 2/1996 |
| WO | 96/37240 | 11/1996 |
| WO | 9637240 | 11/1996 |
| WO | 9803218 A1 | 1/1998 |
| WO | 01/19425 | 3/2001 |
| WO | 01019425 A1 | 3/2001 |
| WO | 2007132485 | 11/2007 |

OTHER PUBLICATIONS

International Preliminary Report on Patentability for PCT/IB2003/004584 filed on Oct. 17, 2003 in the name of Bayco Consulting Limited.

Grilamid Polyamid 12 Technischer Kunststoff fur hochste Anspruche "Grilamid EMS" (EP 03753840) pp. 1-40, ODOCNPL printed Sep. 4, 2009.

Internet Search for Grilamid FE7303; p. 1 of 1, Mar. 24, 2009.

Data Sheet: Chemical Abstract Grilamid FE7303; p. 1 of 1, May 13, 2005.

Opposition against EPO1673114 pp. 1-102; Apr. 2, 2009.

Opposition by Abbott Laboratories Vascular Enterprises Ltd. dated Apr. 2009; 15 pgs. (Citing D9, D10, and D12).

D9—Brochure: Grilamid Poly 12, Technischer Kunststoff für höchstk. Ansprüche; "Grilamid® EMS", Published May 2003; 40 pgs.

D10—Printout: Internet Search for Grilamid FE7303; 1 page, Mar. 24, 2009.

D12—Data Sheet: Chemical Abstracts Grilamid FE7303; 1 page, May 13, 2005.

Patentee's Observations on Notice of Opposition dated Nov. 2009, including Declaration by Botho Hoffman and Provisional Data Sheet on Grilamid FE7303; 21 pgs.

Preliminary Opinion of the Opposition Division dated Sep. 2010; 8 pgs.

Further Submission by Opponent dated Mar. 2011; 3 pgs.

Patentee's Reply to the Summons to Attend Oral Proceeding dated Mar. 2011; 35 pgs.

Rejection of Opposition dated Jul. 2011, including Reasons for Decision and Minutes of Oral Proceedings; 24 pgs.

* cited by examiner

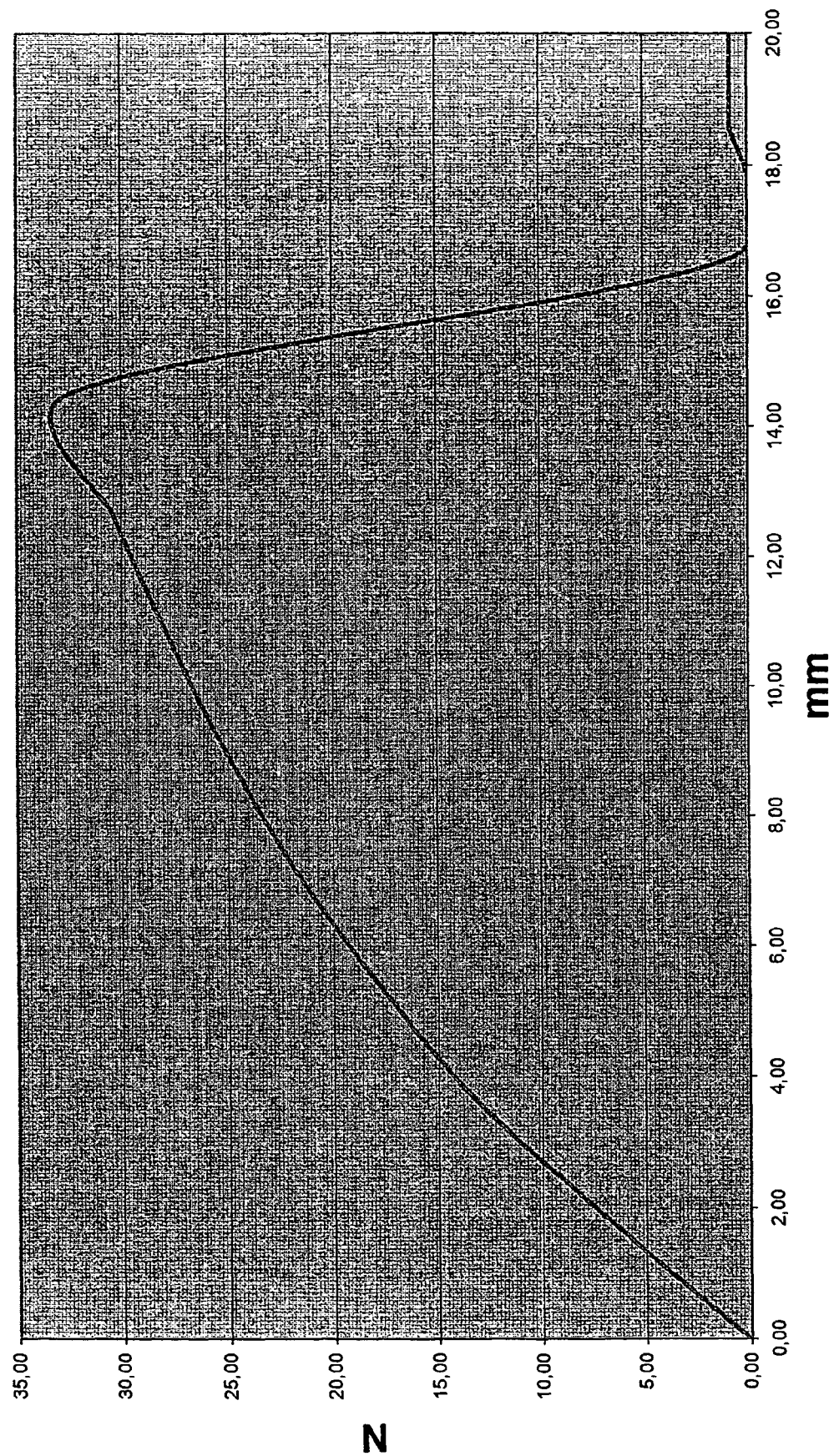

CATHETER BALLOONS

FIELD OF THE INVENTION

The present invention relates to a balloon for medical devices, in particular for a balloon positioned at the distal end of a catheter for use in angioplasty.

BACKGROUND ART

The use of catheters in angioplasty is widely known. A catheter equipped at its distal end with a balloon is moved forward, following a guide wire, until the opening of the narrowed artery is reached. Once the balloon is positioned at the narrowing of the artery, it is repeatedly inflated and deflated. Inflating the balloon and subsequently deflating it inside the artery reduces the amount of narrowing of the arterial duct and restores an adequate blood flow in the cardiac area affected by the stenosis.

The chemical/physical and mechanical characteristics of the plastics material of which the balloon is constituted determine its compliance, that is the adaptability of the balloon to the artery system, and its resistance to stretching, fundamental characteristics for optimum operation of the balloon. The requirements of compliance and strength and the dimensions of the balloon may vary depending on the type of use and the size of the vessel into which the catheter is inserted. The advantages offered by the various polymers are matched to the specific mechanical applications of the balloons.

SUMMARY OF THE INVENTION

The problem addressed by the invention is that of making available a catheter balloon having improved compliance characteristics compared with state of the art balloons.

The subject of the invention is therefore the use of a constituent material for catheter balloons for use in angioplasty, and a balloon manufactured with it, as outlined in the appended claims.

Other characteristics and advantages of the balloon which is the subject of the invention will become clearer from the following detailed description of the invention and from FIG. 1 which follows it and which shows the graph indicating the tensile strength of balloons prepared from polymer material according to the invention.

DETAILED DESCRIPTION OF THE INVENTION

Balloons for use in medical devices according to the invention are formed from block copolymers with polyester-amide blocks. Said polyester-amide polymers are commonly identified by the acronym PEA.

In particular, the polymer material suitable for obtaining a balloon as in the present invention is constituted by monomers forming blocks of polyamide which has been modified with dimer diols and/or with corresponding OH-terminating polyesters containing dimer diols.

Principally, the most common conventional lactams, the amino-carboxylic acids and diamines, may be used to form the polyamide segment. However, the polyamide segment is preferably selected from PA 6, PA 6/6, PA 6/9, PA 6/10, PA 6/12, PA 6/36, PA 11, PA 12, PA 12/12. Moreover, it is preferable to use copolyamides or multipolyamides obtained from $C_2$-$C_{36}$ dicarboxylic acids and $C_2$-$C_{12}$ diamines and also from lactam 6, lactam 12, isophthalic, terephthalic and naphthalene dicarboxylic acid.

More preferably, the polyamide segments are obtained from monomers of $C_6$-$C_{12}$ lactams or from monomers of $C_6$-$C_{12}$ amino-carboxylic acids. The polyamide component may also be obtained from polycondensation of the corresponding salts of the diamines and of the carboxylic acids described above.

The dimer diols used to obtain the polyester-amide polymer are aliphatic dimer diols having a molecular weight of between 400 and 2000, preferably between 400 and 1000. These dimer diols are obtained by conventional industrial methods, including for example the reduction of both the carboxylic groups of a hydrated dimer fatty acid into alcohol groups or by means of the dimerization of unsaturated alcohols. The diols obtained with these technologies always have a certain variable quantity of trimer triols and monofunctional alcohols as by-products. The diol components preferably used in the present invention are $C_{36}$ and/or $C_{44}$ dimer diols with a diol dimer content of at least 90%, a monodiol content of less than 1% and a triol content of less than 5%, and have a hydroxide number of between 195 and 225 mg KOH/g. Still more preferable are dimer diols with a dimer diol content of more than 94% and a monofunctional alcohol and trimer triol content of less than 0.5%.

The OH-terminating diol polyesters constituting the polyamide polymer are obtained from condensation of the above dimer diols with aliphatic and/or aromatic $C_4$-$C_{44}$ dicarboxylic acids. Preferably the hydrated $C_{36}$ dimer fatty acid is used. The preferred diol polyesters have a hydroxide number of between 28 and 90 mg KOH/g, preferably between 50 and 80 mg KOH/g.

The polyamide-polyester polymer used to form the balloons according to the present invention may be prepared using a method with one step or a method with two steps. In the first case, the monomers forming the polyamide blocks are placed in the same reaction reactor with the diol components described above and are condensed, firstly at normal pressure and then at reduced pressure, to give the resulting high molecular weight polyester-amide polymer. The method of synthesizing the polyester-amide polymer comprises two steps: in a first step, the polyamide segment is formed from the polyamide monomers described above and in a second step the polyamide segment thus obtained is combined with the diol components in esterification reaction conditions normally known by a person skilled in the art.

The general chemical formula of the polyester-amide polymers thus obtained may be represented as follows (formula (I)):

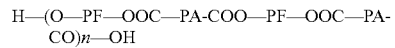

H—(O—PF—OOC—PA-COO—PF—OOC—PA-CO)$n$—OH

In which PA represents the polyamide block while PF is made from the diol block containing dimer diols and/or OH terminating diol polyesters and n is a number between 5 and 20.

The diol component content within the polyester-amide copolymer is 5-50% by weight. Preferably, the diol component concentration is kept within the interval 10 to 30% by weight, still more preferably between 10 and 20% by weight of the total formulation.

The polymers just described above used in the invention to obtain balloons for medical devices are sold, for example, under the brand name Grilamid® by the company Ems-Chemie AG, Switzerland. Particularly suitable examples of commercially available polymers are Grilamid® FE7303 and Grilamid® FE7372. In particular, the polymer Grilamid® FE7303 is formed from polyamide segments deriving from the lauryl lactam with a molecular weight equal to 197 gr/mol and from polyester segments deriving from dimer diol components commercially available under the brand name Pripol® 2033 and Priplast® 3197 respectively with molecular weights equal to 550 gr/mol and 1980 gr/mol, sold by the company Unichema North America, Chicago, Ill., USA. The lauryl lactam component is present in a ratio by weight of 80.2% of the total weight of the final formulation of the copolymer, while the ratios by weight of the diol segments in the final formulation of the copolymer are respectively 12.0% of Pripol® 2033 and 3.7% of Priplast® 3197. In particular, Pripol® 2033 is a diol dimer deriving from a dimer $C_{36}$ fatty alcohol with a molecular weight of 550, a diol component of more than 94.5% and a hydroxide value equal to 200-215 mg KOH/g.

Priplast® 3197 is a diol aliphatic polyester constituted by a $C_{36}$ dimer acid component obtained from dimerization of an unsaturated $C_{18}$ fatty acid and a diol component obtained from hydrogenization of a $C_{36}$ dimeric acid. This specific diol polyester has a molecular weight of 200 and a hydroxide value of between 52 and 60 mg KOH/g.

The polyamide polymer of the general formula (I) is characterized by high flexibility and viscosity, high tensile strength and good resistance to hydrolysis. In particular, the PF blocks deriving from the diol components are responsible for the flexibility and softness of the copolymer, while the PA polyamide blocks give the copolymer hardness, rigidity and crystallinity.

In particular, considering the properties of the copolymer material described above, the insight underlying the present invention is that of utilising these characteristics since they are highly advantageous in the particular application of said polyester-amide copolymers in the use of medical devices, and still more in the particular use of balloons used in angioplasty.

Table 1 below shows the data obtained from a flexibility test carried out on extruded tubes, from which the balloons are subsequently obtained, of polyester-amide material according to the invention. This test confirms the characteristic of high flexibility of the material described above. In particular, the bounce flexibility of tubes for balloons of Grilamid® FE7303 was measured. The test was carried out according to the particulars given by the International Standards Organisation and described in standard ISO 14630: 1997. A tube for a balloon with an outside diameter of 0.9 mm is placed in position by securing it to a support fixture, so as to have a useful length of 0.15 mm. The point of a probe, connected to a force gauge, is placed just touching the surface of said tube-balloon. The probe is moved downwards in contact with the tube and the force necessary to obtain a certain downward movement of the probe is measured. The rate of downward movement of the probe is 20 mm/min. Table 1 below gives the load values (in Newtons) obtained at pre-defined values for downward movement of the probe (from 1 to 8 mm).

TABLE 1

| | Sample | Cross-piece movement | | | | | | | |
| --- | --- | --- | --- | --- | --- | --- | --- | --- | --- |
| | | 1 mm | 2 mm | 3 mm | 4 mm | 5 mm | 6 mm | 7 mm | 8 mm |
| Load (N) | 1 | 0.08 | 0.15 | 0.24 | 0.25 | 0.25 | 0.23 | 0.21 | 0.15 |
| | 2 | 0.09 | 0.19 | 0.25 | 0.25 | 0.26 | 0.23 | 0.21 | 0.16 |
| | 3 | 0.09 | 0.19 | 0.26 | 0.26 | 0.26 | 0.24 | 0.2 | 0.15 |
| | 4 | 0.08 | 0.2 | 0.26 | 0.28 | 0.27 | 0.24 | 0.22 | 0.17 |
| | 5 | 0.07 | 0.17 | 0.25 | 0.26 | 0.25 | 0.24 | 0.23 | 0.17 |
| | Mean | 0.08 | 0.18 | 0.25 | 0.26 | 0.26 | 0.24 | 0.21 | 0.16 |

The table shows a maximum applied load point equal to 0.26 N corresponding to a probe travel equal to 4-5 mm. This value indicates the point of maximum flexibility of the material. This result is particularly significant as it clearly shows the excellent properties of flexibility of the material of the invention, expressed in terms of the elastic elongation of the material.

Moreover, a tube of polyester-amide material of the general formula (I) has a hardness on the Shore D scale of more than 60, a tensile modulus of between 400 and 800 MPa, a tensile load at failure of between 35 and 55 MPa and elongation at failure of approximately 300%. In particular, the preferably used Grilamid® FE7303 has a hardness of 66 on the Shore D scale, a tensile modulus of elasticity of 500 MPa, a tensile load at failure of 40 MPa and elongation at failure of 300%.

The distinctive characteristic of excellent flexibility of the polyester-amide material mentioned above is therefore of particular interest for the application of the material described in balloons for angioplasty. In fact, together with the other characteristics described above of hardness and tensile behaviour, the balloons obtained are characterized by a combination of properties of strength, compliance and softness which characterizes the balloons of the present invention.

The balloons obtained with the polymer material described in the invention certainly have an excellent characteristic of high flexibility and elasticity. Indeed, since the flexibility of a material means the ability of the material to resume its original shape after a deformation has temporarily altered the initial shape, it is immediately apparent that a balloon constituted from highly flexible material will easily withstand the mechanical stresses caused by the repeated action of inflation and deflation required in an angioplasty intervention.

It has moreover been found unexpectedly that the balloon of polyester-amide material which is the subject of the invention has an excellent characteristic of compliance, understood as the percentage increase in the diameter of the balloon as pressure is increased, in addition to an excellent characteristic of adaptability to the arteries and of resistance to stretching.

This combination of the characteristics of good flexibility on the one hand and excellent compliance and strength on the other characterizes the balloons of the present invention and is moreover a combination of properties fundamental to a balloon inserted into the arterial system of a patient during angioplasty treatment.

For the compliance and flexibility tests, 31 samples of balloon with an outside diameter of 3 mm were tested at a nominal pressure of 7 bar, with a double wall thickness equal to 0.04 mm and obtained from the polymer Grilamid® FE7303.

The flexibility test was carried out on a balloon resting at the ends on supports. The probe was positioned in the middle just touching the surface of the balloon. The probe was then moved downwards and the load required to obtain a certain downward movement of the probe was measured. The value for the bending load, measured for a probe travel equal to 4 mm, is 0.25 N. This value confirms the excellent flexibility of the balloons examined, obtained with the new material according to the present invention.

The compliance test is carried out by measuring the increase in diameter (in mm) of the balloons under examination relative to the increase in pressure (in bar) until the burst pressure is reached. Table 2 gives the most significant data obtained from this test. The table shows the data relating to the mean burst pressure recorded, the standard deviation of the measurements carried out and the calculated RBP (Rated Burst Pressure). The value of the Rated Burst Pressure was derived from a probabilistic calculation, in which three times the value of the standard deviation is subtracted from the value of the mean burst pressure measured in the tests on the balloon.

TABLE 2

| | |
|---|---|
| Balloon diameter (mm) | 3.00 |
| Mean wall thickness (mm) | 0.041 |
| Mean burst pressure (bar) | 22.36 |
| Standard deviation | 0.89 |
| Calculated RBP (bar) | 19.67 |

To a person skilled in the art it is immediately evident how the values given in the table are significant for defining the property of the good compliance of the balloons according to the invention. In particular, the burst pressure data obtained above are significant in conjunction with the characteristic of the good flexibility of the balloons. In fact it can be seen that the balloons which are the subject of the invention have a compliance characteristic usually found in far less flexible materials. Moreover, the new balloons described here have a significant advantage of a higher burst pressure and therefore of a higher RBP, in addition to a smaller percentage increase in diameter between the nominal pressure and said RBP, compared with state of the art balloons which have comparable flexibility characteristics.

Moreover, the low standard deviation value calculated on the balloon samples examined demonstrates the high uniformity of behaviour and of the characteristics of the balloons obtained with the new material according to the invention. Furthermore this item of data indicates a high level of reproducibility of the distinctive advantageous characteristics of the balloons which are the subject of the present invention.

Because of its good flexibility, the balloon according to the invention also exhibits better manoeuvrability. In fact the balloon of polyester-amide material exhibits a good ability to follow the track and good adaptation to the path of the vessel. This characteristic therefore also improves the ability to move forward the catheter at the distal end of which the balloon is positioned, along the vascular system until the stenotic lesion is reached. Once the narrowing of the artery is reached, moreover, the good flexibility of the balloon also ensures a better capability for positioning the uninflated balloon at the stenotic obstruction. The better adaptability of the material facilitates the passage of the balloon, uninflated, through the narrowed arterial zone. Finally, this easier passage of the balloon along the path of the vein and through the stenotic lesion means that there is a reduced risk of causing further damage to the vein system concerned and to the stenotic lesion itself.

The good compliance characteristics of the balloon obtained with the polyester-amide material described in the invention mean that said balloons are suitable for an application in therapy of the coronary arteries since the risk of rupture of the vessel as a result of excessive expansion of the balloon is limited.

The good characteristics of flexibility and elasticity of the balloon of the present invention also make it possible to obtain balloons which are advantageously characterized by improved behaviour in returning to the original diameter dimensions after each successive inflation. This enables the same balloon to be inflated a greater number of times and for a longer period. Also deriving from this, moreover, are the good wear characteristics of the balloon. In fact, in normal use of balloons in angioplasty, the burst pressure of the balloon decreases during repeated successive inflations. Contrary to this, the good flexibility of the balloon of polyester-amide material of the present invention improves the ability to maintain the burst pressure determined for the new balloon. This characteristic also allows use of the balloon according to the present invention for a larger number of inflations and for longer periods.

A further advantage of the balloons obtained with the polyester-amide material of the present invention is that they behave well in the tensile test.

In fact, a test was carried out on the balloons of the present invention with the purpose of evaluating the force necessary to cause the balloon to fail under a tensile load. This test too was carried out according to the particulars given by the International Standards Organisation and described in standard ISO 14630: 1997. Thus, for the purpose of testing the failure load of balloons as in the present invention, balloons prepared from Grilamid® FE7303 with an outside diameter of 3 mm, a length of 20 mm and a thickness of 0.04 mm were used. To carry out the test, the balloons are attached at one end to a fixed clamp, and at the opposite end to a movable crosspiece which moves at a rate of 50 mm/min, stretching the balloon until failure occurs. The elongation of the balloon is then calculated, as is the respective yield load until a load peak is reached which represents the point of failure of the balloon and therefore the corresponding failure load. The results obtained from said tensile test on the balloon according to the present invention are shown in FIG. 1, which gives the force-movement graph.

From this test it is found that the balloons of the present invention of polyester-amide material have a failure load value of 32.5 N, which corresponds to a percentage elongation equal to approximately 123%. Comparing these data with those obtained from balloons commonly used in angioplasty, the greater strength and greater elongation capability of the balloons according to the present invention are noted.

Another advantage of using the material described applied to balloons for angioplasty is given by the property of the high viscosity of this material and the ability to maintain a high degree of viscosity even over a period of time. This advantage is reflected particularly in the good slideability characteristics of the material in the process of extrusion to form the tube from which the balloon is then obtained. The copolymer material described in the invention does not therefore require the addition to the polyamide formulation of plasticizing agents to assist in the process.

A further advantage of the polyester-amide material described here is the low absorption of water in aqueous solutions. In fact it is known that polymer substances absorb water and therefore tend to swell. However, the polyester-amide polymers of the present invention, because of low water absorption, do not have a tendency to swell and therefore have a very small increase in weight and volume in aqueous solutions, maintaining their proper shape, volume and dimensions unchanged.

This characteristic is also very advantageous above all in the step of extrusion of the tube from which the balloon is then obtained. In fact, prior to extrusion, all the materials must be placed in an oven to remove the residual moisture present in the granules. A polymer material which has lower water absorption therefore first of all requires a shorter preliminary drying time. Moreover, during the step of extrusion, the tube which emerges from the die is passed through gauging and cooling tanks containing water. The greater the quantity of water which the polymer tube tends to absorb, the greater the risk of formation of microcavities inside the wall of the tube and consequently of microcavities inside the wall of the balloon. These microcavities represent sudden variations in the thickness of the balloon wall and therefore represent potential weak points of failure of the balloon.

It should moreover be noted that the polyester-amide material described in the invention has a high chemical resistance to hydrolysis in an aqueous environment. This chemical stability with respect to hydrolytic degradation contributes to an increased storage life of the balloon obtained from this material, since it ensures that the distinctive mechanical properties of the balloon are maintained over a period of time.

The balloons according to the present invention are manufactured using known techniques for the production of catheter balloons, such as for example the techniques of extrusion of the polymer material, familiar to a person skilled in the art.

The invention is further described by means of the following examples, given by way of illustration and non-limiting, from which the characteristics and advantages of the present invention will become still more evident.

EXAMPLES

Conditions of Extrusion of Tubes for Balloons of the Material According to the Invention Examples 1 and 2 describe tubes for balloons produced by extrusion of the polymer material GRILAMID FE7303. Before extrusion, the pellets of this polymer were dried until the moisture content was less than 0.10%. The tube was extruded at a controlled melting temperature of between 210° C. and 240° C., by means of hot extrusion through five extrusion zones with respectively controlled temperatures. The parameters for the extrusion process were based on the conditions for processing the polymer recommended by the producer of the polymer. After the polymer material was extruded from the die in tube form, it was passed through a small aeration zone in which it was cooled in a bath of deionized water kept at a temperature of approximately 20° C. A manual winch was then used to transport the tube through the water bath. The tube was then cut into 260 mm sections.

Tubes of various sizes were prepared using this method.

Example 1

In this example, balloons 3.00 mm in size, obtained from Grilamid® FE7303, were produced. This polymer has a hardness of 66 on the Shore D scale, a tensile modulus of elasticity of 500 MPa, a tensile load at failure of 40 MPa and elongation at failure of 300%. The sections of tube have an OD value of 0.85 mm and 0.55 mm. To obtain a balloon 3.00 mm in size with a body 20 mm in length, a suitably sized mould was used to allow both the body of the tube and the inside diameter of the central part of the tube to be expanded and inflated to the desired final dimensions. These balloons 3.00 mm in size were obtained with a process temperature of 90° C. and an internal inflation pressure of 28 atm.

The balloons thus obtained underwent a standard bursting test. In particular, the double thickness of the wall of the uninflated balloon was measured. Moreover, the balloon was inflated with successively increasing pressures, so as to measure the outside diameter at each pressure increase until the balloon burst. The results obtained from this test are summarised below in table 3.

Example 2

In this example, balloons 3.50 mm in size, obtained from Grilamid® FE7303, were produced. This polymer has a hardness of 66 on the Shore D scale, a tensile modulus of elasticity of 500 MPa, a tensile load at failure of 40 MPa and elongation at failure of 300%. The sections of tube have an OD value of 0.85 mm and 0.55 mm. The balloons 3.50 mm in size were obtained using the same process as described in example 1, except for the different conditions of temperature and internal inflation pressure. In particular, a process temperature of 100° C. and an internal inflation pressure of 26 atm were used. The results obtained from the bursting test with these balloons are summarised below in table 3.

TABLE 3

| Example | Balloon size (mm) | Thickness of double wall (mm) | Mean burst pressure (atm) | RBP (atm) |
|---------|-------------------|-------------------------------|---------------------------|-----------|
| 1 | 3.00 | 0.032 | 21 | 18 |
| 2 | 3.50 | 0.036 | 20 | 16 |

I claim:

1. A balloon for catheters used in angioplasty, comprising a polyamide copolymer material represented by the general formula (I):

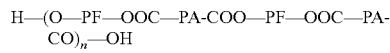

in which PA is a polyamide segment and PF is made from a diol segment comprising OH-terminating dimer dial polyesters and n is a number between 5 and 20.

2. A balloon according to claim 1 in which said diol segment has a molecular weight of between 400 and 2000 g/mole.

3. A balloon according to claim 2 in which said diol segment has a molecular weight of between 400 and 1000 g/mole.

4. A balloon according to claim 1, in which said OH-terminating dimer diol polyesters are obtained from condensation with aliphatic and/or aromatic $C_4$-$C_{44}$ dicarboxylic acids.

5. A balloon according to claim 4 in which the hydroxide value of said diol polyesters is between 28 and 90 mg KOH/g.

6. A balloon according to claim 1 in which the concentration of said diol segment is between 5% and 50% by weight of the total formulation.

7. A balloon according to claim 6 in which the concentration of said diol segment is between 10% and 30% by weight of the total formulation.

8. A balloon according to claim 7 in which the concentration of said diol segment is between 10% and 20% by weight of the total formulation.

9. A balloon according to claim 1, in which said polyamide segment is selected from PA 6, PA 6/6, PA 6/9, PA 6/10, PA 6/12, PA 6/36, PA 11, PA 12, PA 12, PA 12/12.

10. A balloon according to claim 1, in which said polyamide segment is obtained from linear or cyclic, aliphatic or aromatic $C_2$-$C_{36}$ dicarboxylic acids and from aliphatic or aromatic $C_2$-$C_{12}$ diamines.

11. A balloon according to claim 1, in which said polyamide segment is a $C_6$-$C_{12}$ lactam.

12. A balloon according to claim 1, in which said polyamide segment is a $C_6$-$C_{12}$ amino-carboxylic acid.

13. A balloon according to claim 1, in which said polyamide segment is a lauryl lactam.

14. A balloon according to claim 1, wherein the balloon has a diameter of 3 mm at a nominal pressure of 7 bar and a wall thickness of 0.04 mm.

15. A balloon according to claim 1, wherein the balloon has a bending load equal to 0.25 N for a probe travel equal to 4 mm.

16. A balloon according to claim 14, wherein the balloon has a bending load equal to 0.25 N for a probe travel equal to 4 mm.

17. A balloon according to claim 1, wherein the balloon has a calculated mean burst pressure equal to 22.36 bar.

18. A balloon according to claim 1, wherein the balloon has a Rated Burst Pressure equal to 19.67 bar.

19. A balloon according to claim 1, characterized in that it wherein the balloon has a tensile load at failure of 32.5 N and a percentage elongation at failure equal to approximately 123%.

20. A balloon for catheters used in angioplasty, comprising a polyamide copolymer material represented by the general formula (I):

in which PA is a polyamide segment and PF is made from a diol segment comprising OH-terminating dimer diol polyesters and n is a number between 5 and 20, and in which the polyamide copolymer material has a hardness of 66 on the Shore D scale, a tensile modulus of elasticity of 500 MPa, a tensile load at failure of 40 MPa and elongation at failure of 300%.

21. A balloon for catheters used in angioplasty, comprising a polyamide copolymer material wherein in said copolymer polyamide material is represented by the general formula (I):

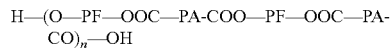

in which PA is a polyamide segment and PF is made from a diol segment comprising OH-terminating dimer diol polyesters and n is a number between 5 and 20 and in which dimer diols of the dimer diol polyesters are $C_{36}$ and/or $C_{44}$ dimer diols, with a diol dimer content of at least 94%.

22. A balloon according to claim 21, wherein the diol polyesters comprise a dimer diol polyester having a molecular weight of 200 and a hydroxide value of between 52 and 60 mg KOH/g.

* * * * *